US00PP25954P2

(12) United States Plant Patent
Tully

(10) Patent No.: US PP25,954 P2
(45) Date of Patent: Sep. 29, 2015

(54) HEBE PLANT NAMED 'TULPINK'

(50) Latin Name: ***Hebe* hybrid**
Varietal Denomination: Tulpink

(71) Applicant: Padraig Tully, Richardstown (IE)

(72) Inventor: Padraig Tully, Richardstown (IE)

(73) Assignee: TULLY NURSERIES, LTD., Richardstown (IE)

( * ) Notice: Subject to any disclaimer, the term of this patent is extended or adjusted under 35 U.S.C. 154(b) by 139 days.

(21) Appl. No.: 13/986,860

(22) Filed: Jun. 12, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV: Plant Variety Database—International Union for the Protection of New Varieties of Plants, Jan. 15, 2015, culitvar name 'Tulpink' (1 page total).*

* cited by examiner

*Primary Examiner* — Susan McCormick Ewoldt
(74) *Attorney, Agent, or Firm* — Penny J. Aguirre

(57) ABSTRACT

A new cultivar of *Hebe*, 'Tulpink', characterized by its compact and rounded plant habit, its foliage that is dark green with a thin red margin and red midrib, its cerise pink flowers and its ability to consistently produce healthy plants.

2 Drawing Sheets

Botanical classification: *Hebe* hybrid.
Cultivar designation: 'Tulpink'.

BACKGROUND OF THE INVENTION

The present invention relates to a new and distinct cultivar of *Hebe*, botanically of hybrid origin and known as *Hebe* 'Tulpink' and will be referred to hereafter by its cultivar name, 'Tulpink'. 'Tulpink' is grown for use as a container plant and as a landscape shrub.

The new cultivar was selected as a seedling that arose from the open pollination of unnamed proprietary *Hebe* plants (not patented) from the Inventor's breeding program growing in a trial garden in the Inventor's nursery in summer of 2007 in Ballyboughal, Dublin County, Ireland. The parentage is unknown as seeds had been collected and sown from many female plants.

Asexual propagation of the new cultivar was first accomplished by the Inventor by softwood cuttings in Ballyboughal, Dublin County, Ireland in summer of 2007. Asexual propagation by softwood stem cuttings has been determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Tulpink' as a new and distinct cultivar of *Hebe*.

1. 'Tulpink' exhibits a compact and rounded plant habit.
2. 'Tulpink' exhibits foliage that is dark green with a thin red margin and red midrib.
3. 'Tulpink' exhibits cerise pink flowers.
4. 'Tulpink' consistently produces healthy plants.

'Tulpink' can be most closely compared to the cultivars 'Inspiration' and 'Wiri Charm' (both un-patented). 'Inspiration' differs from 'Tulpink' in having a more upright plant habit, in having foliage that is lighter green in color and narrower, in having flowers that are mauve pink, and in being taller in height. 'Wiri Charm' differs from 'Tulpink' in having foliage that is narrower, longer, and lighter green in color, in having a more vigorous growth habit, and in having a taller and more upright plant habit.

BRIEF DESCRIPTION OF THE DRAWINGS

The accompanying colored photographs illustrate the overall appearance and distinct characteristics of the new *Hebe*. The photographs were taken of a plant approximately five years in age as field grown in Stroe, The Netherlands.

The photograph in FIG. 1 is a side view of 'Tulpink'.

Figure 1:
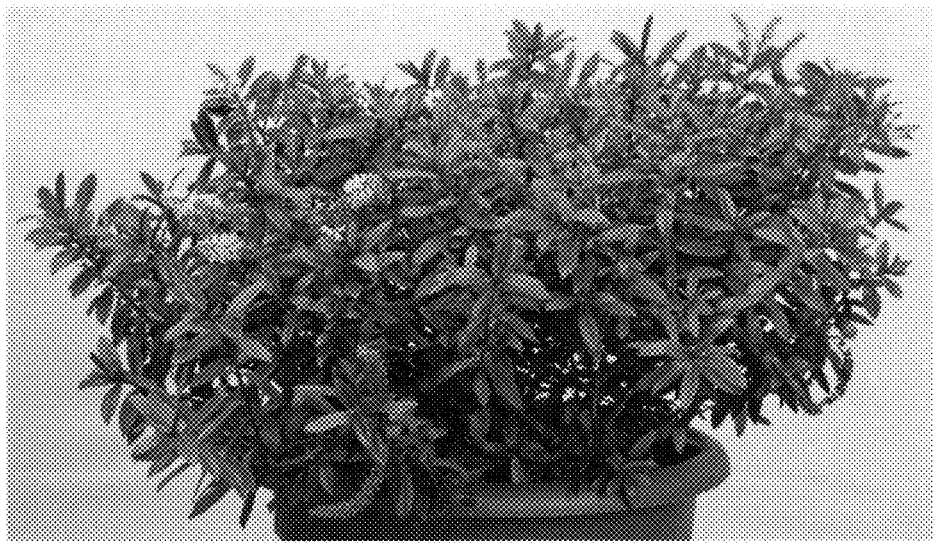
Figure 2:
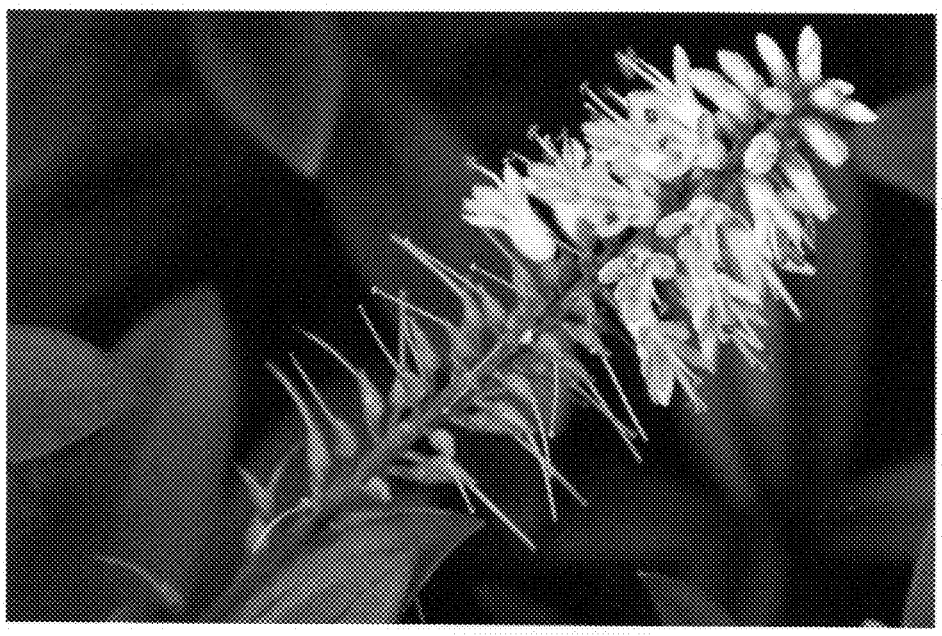

The photograph in FIG. 2 provides a close-up view of an inflorescence of 'Tulpink'.

Figure 3:
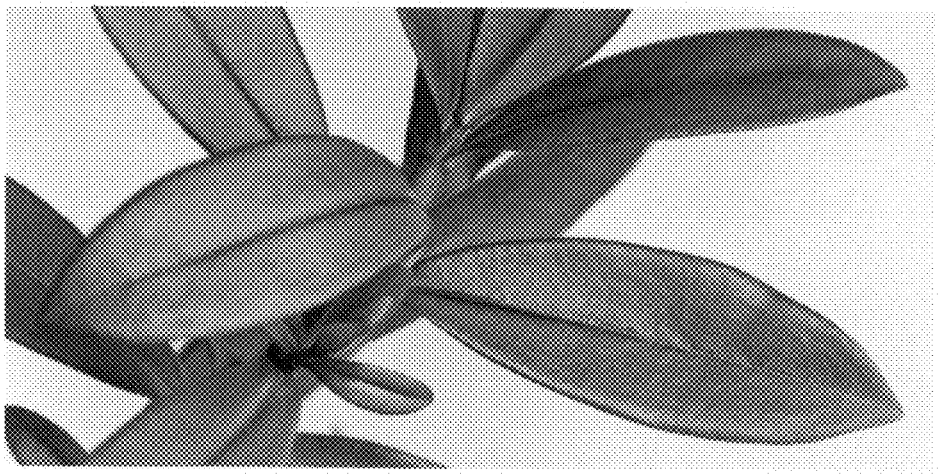

The photograph in FIG. 3 provides a close-up view of the foliage of 'Tulpink'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of five year-old plants of the new cultivar as field grown in Stroe, The Netherlands. Plants were grown under average day temperatures of 10° to 28° C. and average night temperatures of 4° to 16° C. The phenotype of the new cultivar may vary with variations in environmental, climatic, and cultural conditions, as it has not been tested under all possible environmental conditions. The color determination is in accordance with The 2007 R.H.S.

Colour Chart of The Royal Horticultural Society, London, England, except where general color terms of ordinary dictionary significance are used.

General plant characteristics:

*Plant type.*—Evergreen shrub.

*Plant habit.*—Compact and rounded.

*Flowering period.*—Continuously from late June to late September.

*Height and spread.*—Reaches about 37 cm in height and 75 cm in spread.

*Cold hardiness.*—At least tolerant to U.S.D.A. Zone 8.

*Disease resistance.*—Not more susceptible to pests and diseases than other *Hebe* varieties.

*Root description.*—Fibrous to slightly fleshy.

Growth and propagation:

*Growth rate.*—Moderate.

*Propagation type.*—Softwood stem cuttings.

*Root initiation.*—About 28 days at 18° C.

*Root development.*—About 120 days to fully develop a liner.

Stem description:

*Stem size.*—Lateral branches are an average of 13.5 cm in length and 2 mm in width.

*Stem shape.*—Round.

*Stem color.*—Young stem; 197A to 197B, older bark; 199B.

*Stem surface.*—Smooth, slightly glossy.

*Stem strength.*—Strong.

*Internode length.*—Average of 1.0 cm.

*Branching habit.*—Very freely branched from base, average of 110 lateral branches.

Foliage description:

*Leaf shape.*—Narrow obovate to narrow elliptic.

*Leaf division.*—Single.

*Leaf base.*—Attenuate-cuneate.

*Leaf apex.*—Acute.

*Leaf venation.*—Pinnate, only main vein clearly visible, other veins hardly visible, upper surface; N186C in color, lower surface; 146A in color.

*Leaf margins.*—Entire.

*Leaf attachment.*—Sessile.

*Leaf arrangement.*—Opposite.

*Leaf surface.*—Glabrous, upper surface glossy, lower surface very slightly glossy.

*Leaf color.*—Upper young surface; a blend of 141A and 143A, mature upper surface; a blend of N137A and 147A with narrow margin N186C, lower young surface; a blend of 144A and 146B, mature lower surface; a blend of 144A and 146A, closest to 146A with narrow margin N186C.

*Leaf number.*—Average of 28 per lateral branch.

*Leaf size.*—4.6 cm in length and 1.3 cm in width.

*Leaf aspect.*—Held nearly horizontal to slightly upright to stem.

*Leaf fragrance.*—None.

Flower description:

*Inflorescence type.*—Raceme.

*Inflorescence size.*—10.1 cm in length and 2.4 cm in width.

*Inflorescence lastingness.*—About 7 days, self-cleaning.

*Flower shape.*—Campanulate.

*Flower fragrance.*—None.

*Flower quantity.*—Average 85 florets per inflorescence.

*Flower arrangement.*—Axillary racemes.

*Flower aspect.*—Outward.

*Flower size.*—Average of 9 mm in depth and 5 mm in diameter.

*Peduncles.*—Strong strength, 9.5 cm in length and about 1.5 mm in diameter, a blend of 148A and 197B, held at about a 50° angle to lateral branch.

*Pedicels.*—Strong strength, average of 2 mm in length and 0.75 mm in diameter, held at about a 60° to peduncle, a blend of 148A and 197C in color.

*Flower buds.*—Narrow elliptic, 6 mm in length and 2 mm in diameter, 64C in color, base a blend of 69D and N155A.

*Calyx.*—Rotate-shaped, average of 2 mm in length and 2 mm in diameter.

*Sepals.*—4, ovate in shape with entire margins, arrangement; rotate and campanulate, acute tip, base cuneate with lower 50% fused, dull and smooth surface, color of young and mature upper and lower surfaces 143A, average of 2 mm in length and 1 mm in width.

*Petals.*—Average 4, oblanceolate in shape and lower fused, about 7 mm in length and 2 mm in width, entire margins, apex broad acute, upper and lower surface is dull and glabrous, color of upper surface when opening; N74B to N74C with 157D base and lower surface when opening; 75A with 157A base, color of upper and lower surface when fully open; 75A with N155A base, both surfaces non-fading.

Reproductive organs:

*Gynoecium.*—1 Pistil, 8.5 mm in length, stigma is clavate in shape and N170D in color, style is about 8 mm in length and 70B to 70D towards base in color, ovary is 143A to 143B in color.

*Androcoecium.*—2 stamens, anthers are dorsifixed, elliptic in shape, 2 mm in length and 72B in color, filaments are about 8 mm in length and NN155D in color, pollen is low to moderate in quantity and 156C to 156D in color.

*Fruit and seed.*—280 fruits per lateral branch, 3 mm in length and 2 mm in diameter, smooth, dull surface, 200D in color, seeds very small, less than 0.2 mm in length and diameter, 199C to 199D in color.

It is claimed:

1. A new and distinct cultivar of *Hebe* plant named 'Tulpink' as herein illustrated and described.

* * * * *